(12) United States Patent
Matsen et al.

(10) Patent No.: US 7,705,725 B2
(45) Date of Patent: Apr. 27, 2010

(54) METHODS AND SYSTEMS FOR MONITORING STRUCTURES AND SYSTEMS

(75) Inventors: Marc R. Matsen, Seattle, WA (US); Gary E. Georgeson, Federal Way, WA (US); Everett Westerman, Auburn, WA (US); Kenneth Porad, Tacoma, WA (US); Arun Ayyagari, Seattle, WA (US); Kevin Ung, Bellevue, WA (US); Craig Farris Battles, Seattle, WA (US); David Blackwell, Seattle, WA (US)

(73) Assignee: The Boeing Company, Chicago, IL (US)

( * ) Notice: Subject to any disclaimer, the term of this patent is extended or adjusted under 35 U.S.C. 154(b) by 667 days.

(21) Appl. No.: 11/620,871

(22) Filed: Jan. 8, 2007

(65) Prior Publication Data
US 2008/0167833 A1     Jul. 10, 2008

(51) Int. Cl.
*G08B 23/00* (2006.01)
(52) U.S. Cl. ...................................... 340/529
(58) Field of Classification Search ................. 340/529, 340/505, 517, 10.1, 825.69, 945; 702/34, 702/35
See application file for complete search history.

(56) References Cited

U.S. PATENT DOCUMENTS

| | | | |
|---|---|---|---|
| 5,774,376 A | 6/1998 | Manning | |
| 6,009,356 A | 12/1999 | Monroe | |
| 7,343,265 B2 * | 3/2008 | Andarawis et al. | 702/188 |
| 2002/0016654 A1 * | 2/2002 | Ing et al. | 701/29 |
| 2006/0106550 A1 * | 5/2006 | Morin et al. | 702/34 |
| 2006/0170535 A1 * | 8/2006 | Watters et al. | 340/10.41 |
| 2006/0176179 A1 | 8/2006 | Skorpik et al. | |
| 2006/0179949 A1 * | 8/2006 | Kim | 73/588 |
| 2006/0254366 A1 | 11/2006 | Williamson et al. | |
| 2006/0259217 A1 | 11/2006 | Gorinevsky et al. | |

FOREIGN PATENT DOCUMENTS

| | | |
|---|---|---|
| WO | 98/40711 | 9/1998 |
| WO | 0025272 A | 5/2000 |
| WO | 0201172 A | 1/2002 |

OTHER PUBLICATIONS

International Search Report No. PCT/US2007/087276; Jun. 30, 2008; 17 pages.

* cited by examiner

*Primary Examiner*—Phung Nguyen
(74) *Attorney, Agent, or Firm*—Armstrong Teasdale LLP

(57) ABSTRACT

Methods and systems for structural and component health monitoring are provided. A system includes a plurality of sensor systems positioned about an object to be monitored and a processing system communicatively coupled to at least one of said plurality of sensor systems wherein the processing system includes an ontology and reasoning module configured to model the object to be monitored, reason about the received sensor data associated with the object to be monitored and reason about the relationships between the received sensor data to fuse the data into contextual information for the overall object to be monitored and a contextual analyzer configured to transmit the received sensor data to said ontology and reasoning module and to store the information into a contextual information database.

25 Claims, 4 Drawing Sheets

METHODS AND SYSTEMS FOR MONITORING STRUCTURES AND SYSTEMS

BACKGROUND OF THE INVENTION

This invention relates generally to structure and system health monitoring and more particularly, to methods and systems for monitoring structure and system health using networked smart wireless sensor devices.

At least some known applications for wireless communication networks include industrial control and monitoring, intelligent agriculture, asset and inventory tracking, and security. Typical wireless sensing systems comprise wireless sensors that passively gather large amounts of data from an environment, which is typically transmitted to a host node for evaluation by an individual specifically trained to manually evaluate the information as time permits. This typical sensor system sometimes includes conversion of the signal from analog to digital and/or signal conditioning. The raw time-series data is typically transmitted in its entirety to a host node where it is sometimes stored indefinitely and analyzed very infrequently.

A conventional system comprises a plurality of sensors coupled to an interface which sends the information via a wired, large bandwidth transmission to a computer at a remote location. Installation of the wires themselves are cost-prohibitive due to the distances over which the wires must pass, weight prohibitive due to the amount of the wiring, or infeasible in many other situations due to the environment where the sensor itself and respective wiring are located. Low-power wireless technology has proved to be an enabler for wireless sensing in areas that were previously unattainable, due to the 'difficult-to-reach' or 'difficult-to-wire' nature of the installation or retrofit process. However, transmitting the raw data via a large bandwidth wireless system may consume significant amounts of power and create unnecessary network traffic.

Preprocessing is sometimes used to reduce the amount of network traffic using compression technology or by intelligently sending only the most pertinent data. However, reducing the data available for analysis also reduces the effectiveness of the analysis.

BRIEF DESCRIPTION OF THE INVENTION

In one embodiment, a system for structural and component health monitoring includes a plurality of sensor systems positioned about an object to be monitored and a processing system communicatively coupled to at least one of the plurality of sensor systems. The processing system includes an ontology and reasoning module configured to model the object to be monitored, reason about the received sensor data associated with the object to be monitored and reason about the relationships between the received sensor data to fuse the data into contextual information for the overall object to be monitored. The processing system further includes a contextual analyzer configured to transmit the received sensor data to the ontology and reasoning module and to store the information into a contextual information database.

In another embodiment, a method of monitoring the health of structures and system components includes positioning a plurality of sensor systems proximate an object to be monitored wherein the sensor systems each include one or more sensors configured to detect object data that is related to the object health. The method also includes wirelessly transmitting the data to at least one of another one of the plurality of sensor systems and a processing system, and analyzing the data to determine a contextual relationship between each of the plurality of sensor systems and the received data such that a present state of the object is determined.

In yet another embodiment, a sensor networking system for monitoring the health of an aircraft structure and system components related to the aircraft includes a plurality of sensor systems positioned about the aircraft. The sensor systems include a flexible substrate, an energy harvesting system, a rechargeable battery, and a microprocessor that controls wireless communication between at least one of the sensor systems and a processing system remote from the plurality of sensor systems, the plurality of sensor systems further including sensors including a plurality of different modalities. The system also includes a processing system communicatively coupled to at least one of the plurality of sensor systems, the processing system configured to receive at least one of sensor data and fused sensor data the processing system including a situation awareness analyzer configured to determine an overall present state of the aircraft by observing the events and activities within the aircraft structure and aircraft systems and correlating individual data elements and behavioral models to deduce overall system state and behavior.

DETAILED DESCRIPTION OF THE INVENTION

Figure 1:
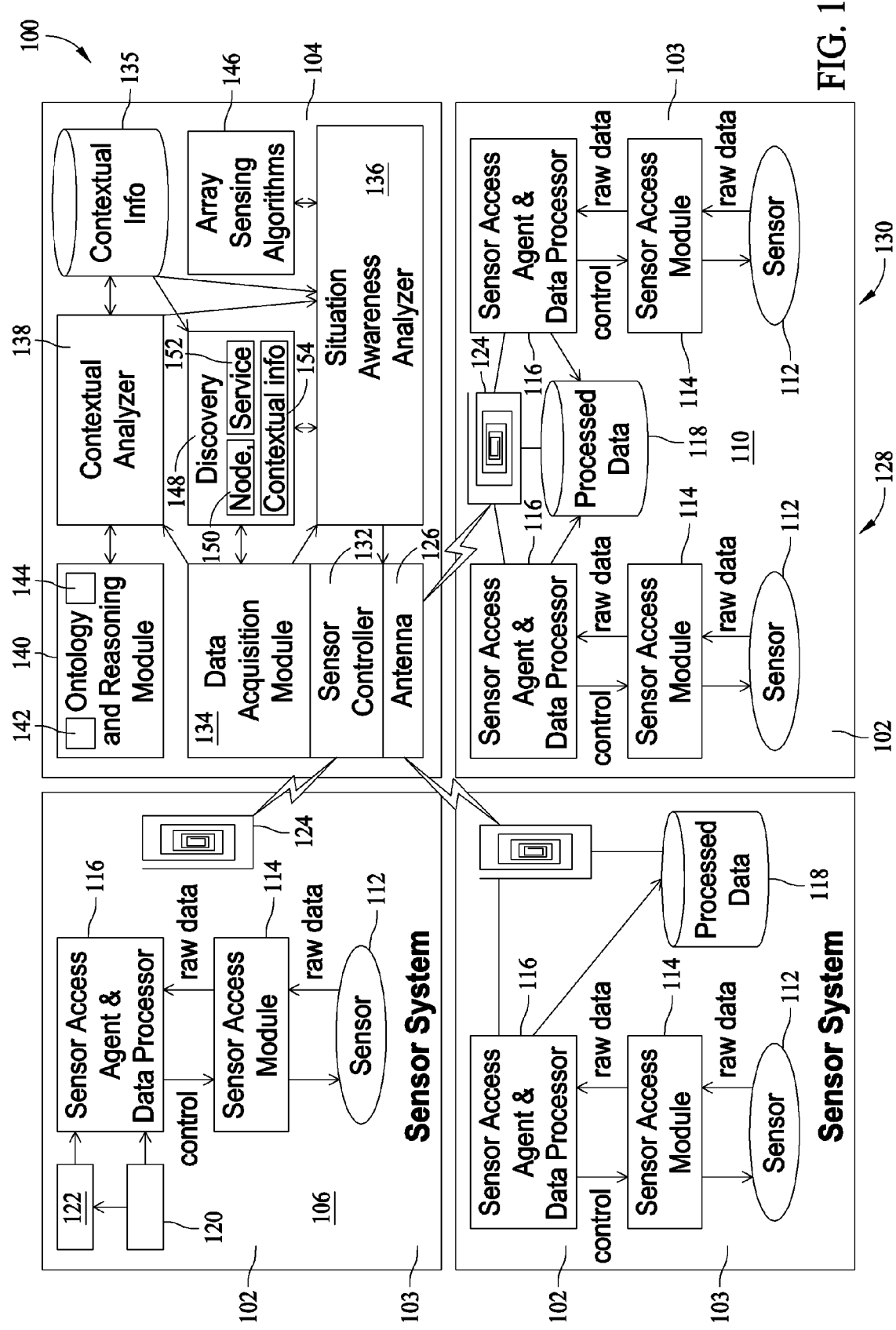
FIG. 1 is schematic block diagram of a Structure and Systems Health Monitoring System (SSHMS) in accordance with an exemplary embodiment of the present invention.

FIG. 1 is schematic block diagram of a Structure and Systems Health Monitoring System (SSHMS) 100 in accordance with an exemplary embodiment of the present invention. In the exemplary embodiment, SSHMS 100 includes at least one sensor system 102 and at least one onboard processing system 104. Sensor system 102 may include a variety of sensor system types. For example, a single sensor system 106 may include only a single sensor and may not include an onboard storage memory capability. A memory sensor system 108 may include a single sensor and an onboard storage memory for relatively long term storage of data. A multi-sensor system 110 may include a plurality of sensors and may include an onboard storage memory for relatively long term storage of data.

In the exemplary embodiment, sensor systems 102 generally include a sensor 112, a sensor access module 114, and a sensor access agent and data processor 116. Sensor systems 108 and 110 also include an onboard memory 118 for storing raw or processed data, swappable program instruction code, and look-up tables (LUT), as needed to perform the various functions of sensor systems 102. Sensor systems 102 include relatively thin lightweight energy harvesting materials 120 connected to wafer thin polymer based or lithium ion rechargeable batteries 122 to power embedded microprocessors. In addition, these individual microprocessors 116 and integrated micro-sensors 112 are attached to a thin planar antenna 124.

Sensor systems 102 include small lightweight sensors 112 with embedded local micro-processing for collecting, deciphering and recording data along with wireless communication capability. Sensor systems 102 provide specific environmental and performance data for the components, structure, and systems that encompass an entire vehicle wide component set. Such data, when integrated, permits a detailed understanding of the relationship between the performance and environment of each component, and how that relationship impacts the overall health of the set of components that make up the entire airplane. Sensor systems 102 include a flexible substrate 103 that is backed by a self-adhesive layer for attachment to a component or structure of interest.

Sensor systems 102, which combine energy harvesting and storage and micro-processing record information such as but not limited to impact, thermal conditions, corrosion, moisture, electrical parameters, load, dynamic cycles, and combinations including any of the above, directly to the data processors 116 as generated by the integrated micro-sensors 112. Data processors 116 include on-chip memory for storing the sensor data and control features that control wireless communication between sensor systems 102 and/or onboard processing system 104. In the exemplary embodiment, sensor systems 102 are mounted on appliqué for ease of application and removal for the structural applications and are integrated into the name plate for the individual systems based components.

Sensor access module 114 provides wrapper functions for underlining sensor 112. The wrapper function provides a consistent interface, for example, but is not limited to an Application Programming Interface (API), to the upper layers of sensor access agent and data processor 116, to control and retrieve data from sensor 112. The sensor access agent and data processor 116 is the service entity supporting retrieval of sensor data via a set of pre-defined common interfaces that onboard processing system 104 can invoke. The data processor performs the first tier data fusion of raw sensor data into a preliminary form of contextual information. The degree of data fusion performed by the data processor depends on the type of sensor and the complexity of the sensor system. For example, data processors in sensor system 110 support the fusion of data retrieved from a first sensor subsystem 128 and a second sensor subsystem 130 into a coherent form and representing the information in a form that is relevant to sensor system 110 context at the time the data is sensed. This information, along with the raw sensor data, is stored within local storage device 118. The stored information can be retrieved by onboard processing system 104 at a later time for decision support system application or as a log history to monitor the behavior of sensor system 110.

Onboard processing system 104 may receive sensor data for various structural and system components and combine different types of sensor data (regardless of the source and regardless of the component or event being monitored) to generate a more accurate assessment of the structural and system health of the specified component.

Onboard processing system 104 is configured to process the sensor data along with any historical data and pre-defined contextual information to determine or generate a contextual assessment of the condition and/or status of the structure and system. Onboard processing system 104 receives sensor data from one or more structural or system components and combines this data, potentially from different sensor types, to make a more complete condition estimate for the specified component and/or the system as a whole. Onboard processing system 104 may process historical data for trending purposes.

Onboard processing system 104 may also receive any amount of manual inspection data or manual inspection data may be processed after download of the onboard processing system 104 data to a central server. As used herein, "manual inspection data" is data that has been collected with human labor, as opposed to data that has been collected via an automated system. Although one preferred embodiment of Structure and Systems Health Monitoring System (SSHMS) 100 eliminates the need for manual inspection data, Structure and Systems Health Monitoring System (SSHMS) 100 is capable of processing such data if it is available. Structure and Systems Health Monitoring System (SSHMS) 100 is capable of merging manual inspection data with automated sensor data.

Onboard processing system 104 is configured to perform any number of suitable data fusion techniques during the processing of the sensor data and optional manual inspection data. Onboard processing system 104 processes its input data in an intelligent manner to generate a more complete, and generally more reliable and accurate assessment of the structural health of the monitored component. Onboard processing system 104 utilizes techniques including but not limited to, expert systems, neural networks, and artificial intelligence technologies. Onboard processing system 104 is also configured to perform data trending to filter noise from the sensor data and to otherwise enhance the accuracy of the health assessment. For example, onboard processing system 104 performs time domain and spatial filtering of the sensor data. Data trending functionality includes but is not limited to smoothing, for example, providing an accurate estimate of the past history of the sensor data assessment, filtering, for example, computing an accurate noise rejecting estimate of the current structural and systems health state taking into account past history data, and/or prediction, for example, projecting the sensor data evolution into the future.

The data is recorded on the microprocessor and then intermittently relayed to an onboard processing system 104 by an embedded rule-based agent. The migration of the data from data processors 116 to the individual onboard processing systems 104 populated across the entire critical component family of the airplane, both structural and systems, including propulsion, provides the smart characteristics of memory, data manipulation, and wireless communication, to SSHMS 100. Onboard processing system 104 includes a small externally or internally mounted transmit/receive antenna 126 depending on the location of the sensor systems 102. In the exemplary embodiment, antenna 126 utilizes UHF or SHF band frequencies. Antenna 126 sends out a signal to the various sensor systems 102 currently of interest. The identified sensor system 102 energizes its wireless communication circuit and transmits the information of interest via energy emitted by the attached thin planar antenna 124 using power from the integrated thin integrated rechargeable battery 122. Sensor systems 102 are intermittently interrogated to download the sensor data to the on-board repository.

Onboard processing system 104 monitors, records, and appropriately generates notification alerts with accurate information on a real time basis. In the exemplary embodiment, onboard processing system 104 includes seven major components and is designed to function remotely from sensor system 102. In the exemplary embodiment, onboard processing system 104 executes on an independent computing system. In an alternative embodiment, onboard processing system 104 is collocated with another on-board computing system. Sensor controller 132 permits a data acquisition module 134 to retrieve real time and historical sensor data and contextual information 135 from sensor system 102. The real time sensor data interrogation involves the establishment of either a synchronous TCP socket connection from sensor controller 132 to the sensor access agent 116, or an asynchronous TCP socket connection from the sensor access agent to sensor controller 132. In addition, sensor controller 132 can also retrieve historical sensor data and sensor contextual-information from the sensor's local-store 118.

Selection of the specific sensor system 102 to be interrogated, or retrieval of historical data, and the interrogation periodicity are controlled by a situation awareness analyzer 136. Once the data is received, data acquisition module 134 publishes or transmits the received data/information to a contextual analyzer 138 and situation awareness analyzer 136. Contextual analyzer 138 uses the data as an input object for an ontology and reasoning module 140 to fuse the data into contextual information for the overall airplane system and subsequently store the information into the contextual information database 135. Ontology and reasoning module 140 includes an ontology engine 142, which comprises a data model representing a domain such as the entire aircraft or a smaller defined portion of the aircraft and is used to reason about the objects in that domain and their inter-relationships. The objects may be defined as for example, but not limited to components, systems or structures that make up the aircraft or the aircraft environment. A reasoning module 144, which is the reasoning rule engine, is used to reason the relationships.

An array sensing algorithm module 146 includes logic that governs the order in which specific sensor systems 102 are interrogated and the periodicity of their respective interrogations. This logic is fed into the situation awareness analyzer 136 in order to direct sensor controller 132. In addition to the logic from array sensing algorithm module 146, situation awareness analyzer 136 also uses discovery module 148 to determine which sensor systems 102 to interrogate. In the exemplary embodiment, discovery module 148 includes three stages, a node discovery 150, which determines the presence of a node for example, sensor system 102, a service discovery 152, which discovers the service provided by the given node, and a contextual information discovery 154, which discovers information relevant to the current context.

Situation awareness analyzer 136 provides a single picture of the present state of the airplane system so that it can monitor, record, and appropriately generate notification alerts with the proper information in real time. In order to accomplish this and compile an overall view of the current state, situation awareness analyzer 136 needs to be aware of the current and past contextual information generated by the contextual analyzer 138, discovery information from the discovery module 148, logic from the array sensing algorithm module 146, data reported by the data acquisition module 134, and retrieve required sensor data to further augment the overall view.

This architecture creates a record of the environment and the performance of each of the critical components of the airplane during flight. These records would be used to construct correlations between the interaction between the flight-environment/structural-performance and the subsequent systems performance. In addition, the reciprocal of this would also be utilized, where the system performance impacts the flight characteristics and structural behavior of the airplane. From this integrated data set, algorithms are dynamically adjusted and/or new algorithms constructed that provide input to design improvements, flight conditions to avoid and the construction of detailed and customized maintenance activities for individual airplanes based not only on the family of individual parts installed but also on the anticipated use of the airplanes.

Integrated vehicle health monitoring using Structure and Systems Health Monitoring System (SSHMS) 100 includes a large number of distributed sensor systems 102 communicatively coupled into a network or a plurality of interconnected networks. Such a sensor network improves the situational awareness of the vehicle state that includes its system and sub-system assemblies over the duration of product life. However, the large number of sensors within the vehicle requires data from these disparate and heterogeneous sensors to be processed and combined intelligently to determine a clear and unambiguous view of the vehicle state that is temporally relevant for maintenance and planning decision support systems. Data from the individual sensor systems 102 is intelligently analyzed to extract information and the information from multiple sensor systems 102 utilizing sensors 112 of different modalities is intelligently combined to create a fused situational awareness view of the overall vehicle state. Intelligent information is extracted from sensor data and fused from multiple modalities to provide an overall view of the vehicle system and sub-system states. Events and activities within systems and sub-systems are observed and individual data elements and behavioral models are correlated to deduce overall system state and behavior. The correlation of individual data elements and behavioral models within temporal space also enables estimating the states of the system and sub-systems for pro-active decision support systems. The estimated state can include any future anticipated state which may be caused by events and activities that have happened in the related environment. The sensor networks are arranged for distributed monitoring with low-power devices and ad hoc wireless networking capability to inter communicate with onboard processing system 104. Sensor systems 102 include adaptive storage functions by appropriately fusing the sensed data to ensure that it can effectively be communicated to onboard processing system 104. Data reduction at the sensor source minimizes the communication requirements thereby easing the power requirements of the overall system since computation is more power efficient when compared to communication. Structure and Systems Health Monitoring System (SSHMS) 100 optimizes a balance between local computation versus communication while ensuring the required information quality is retained to enable onboard processing system 104 to function effectively regardless of data fusion at the sensor sources or at intermediary aggregation points. Array sensing algorithms 146 and sensors 112 that incorporate directional sensing capabilities provide a more complete view of the system and sub-systems in particular areas. Local reasoning is incorporated into the sensor source to enable time and space based analysis to measure the sensor viewpoint for the event. The sensor sources include power-aware computation to minimize the volume of data stored onboard the sensor device and communicated to onboard processing system 104.

Figure 2:
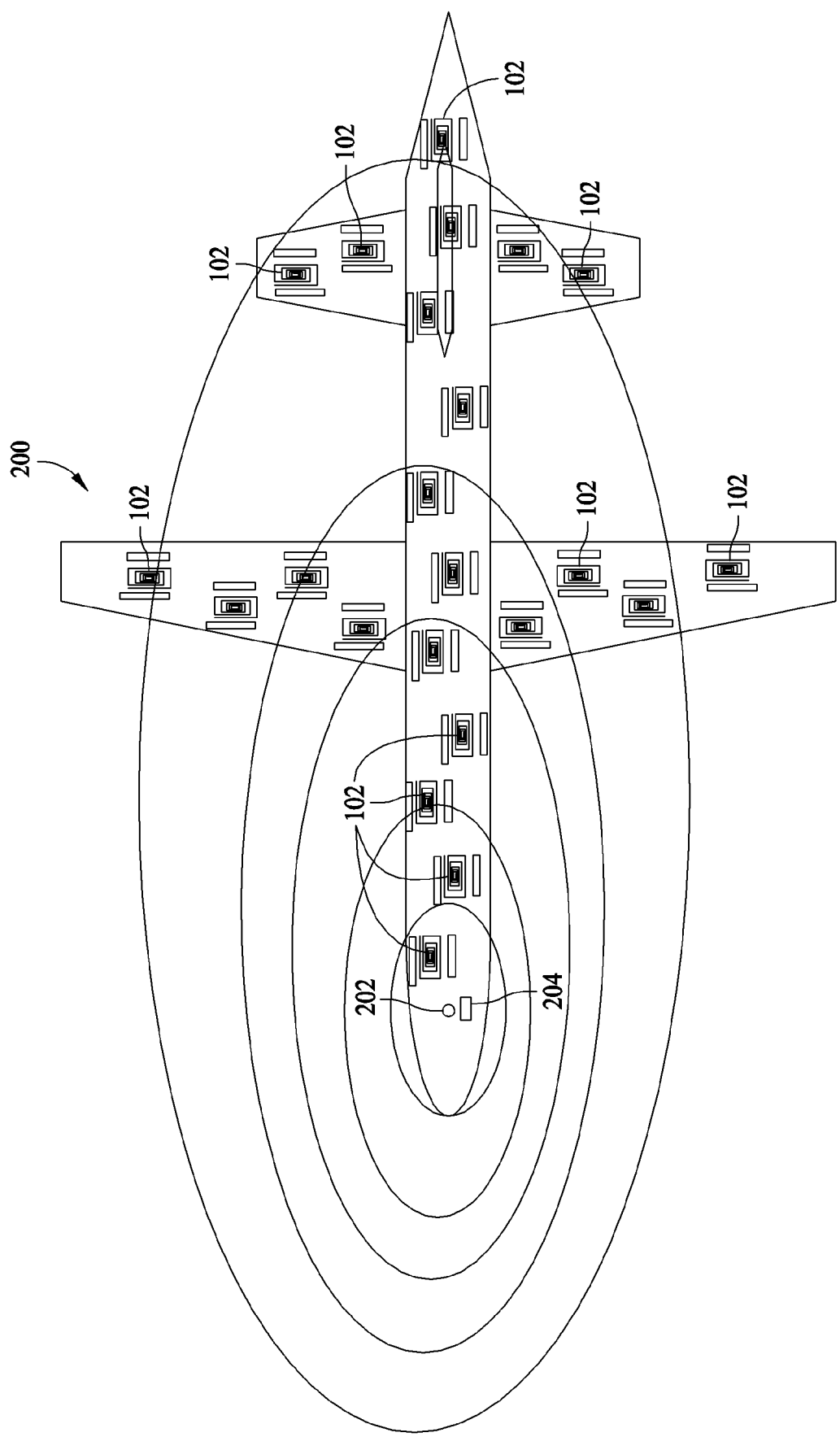
FIG. 2 is a plan view of an aircraft including a Structure and Systems Health Monitoring System (SSHMS) in accordance with an exemplary embodiment of the present invention.

FIG. 2 is a plan view of an aircraft 200 including a Structure and Systems Health Monitoring System (SSHMS) 100 in accordance with an exemplary embodiment of the present invention. Aircraft 200 comprises generally a framework structure covered by an aerodynamic skin. During various flight operations, the structure and skin are subject to compressive, bending, torsional, and tensile static or fatigue loads due to propulsive and drag forces and thermo-dynamic expansion and contraction of the components of the structure and the skin. Such loads over time may weaken or damage the stressed components and structures. Periodic inspections are relied on to discover the precursors of failure so that maintenance may correct problems prior to a catastrophic failure that damages aircraft 200 or impacts scheduling aircraft 200 for normal flight duty.

Structure and Systems Health Monitoring System (SSHMS) 100 includes a plurality of sensor systems 102 applied to structural members and skin sections of aircraft 200. A reader 202 including a transmit/receive antenna 204 is positioned to transmit an interrogation signal to one or more of sensor systems 102. Each sensor system 102 responds to the interrogation signal with the information requested by reader 202. Reader 202 may request raw data or data that has been primarily processed by sensor system 102, or may request stored data stored in storage device 118. In the exemplary embodiment, reader 202 comprises an onboard processing system 104 described above. In an alternative embodiment, reader 202 comprises a relay device configured to receive data from one or more sensor systems 102 and relay the data to an onboard processing system 104 positioned remotely on aircraft 200. In the exemplary embodiment only one reader 202 is shown, however additional readers 202 and/or onboard processing systems 104 may be included in Structure and Systems Health Monitoring System (SSHMS) 100. In the exemplary embodiment, sensor systems 102 are selected and placed to monitor structural characteristics of the operation of aircraft 200. Such sensor systems 102 may include vibration sensors, strain sensors, temperature sensor, and other sensors configured to sense conditions associated with the operation of aircraft 200.

Figure 3:
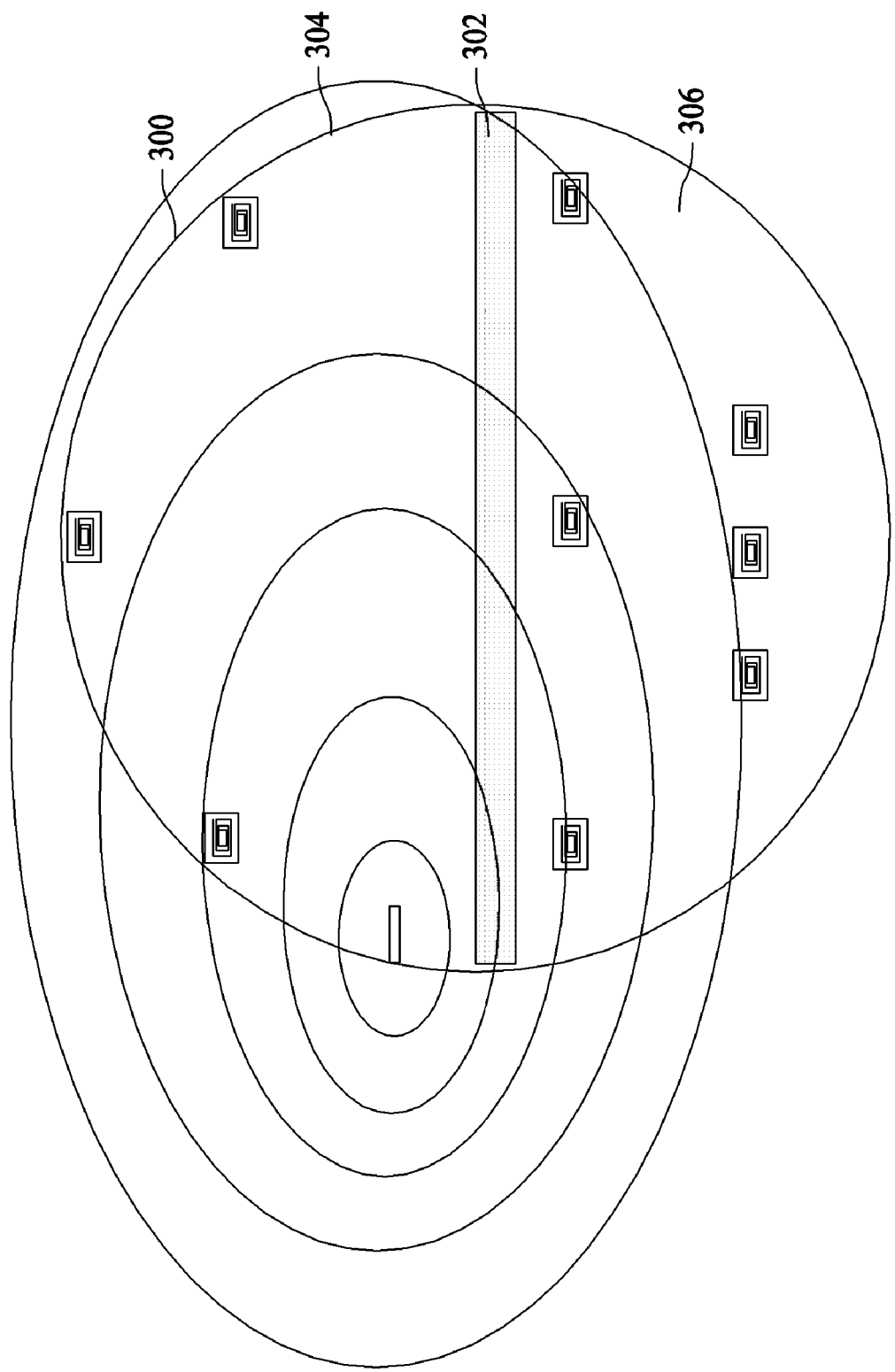
FIG. 3 is a cross-sectional view of a portion of a fuselage of the aircraft shown in FIG. 2.

FIG. 3 is a cross-sectional view of a portion of a fuselage 300 of aircraft 200 (shown in FIG. 2). In the exemplary embodiment, fuselage 300 includes a passenger floor 302 dividing fuselage 300 into an upper passenger 304 compartment and a lower cargo compartment 306. A reader 308 is positioned such that wireless communication signals transmitted from reader 308 are capable of being received by a plurality of sensor systems 102. Sensor systems 102 are positioned on for example, but not limited to passenger compartment equipment, passenger carry-on stowage bins, in the vicinity of passenger seating, and system components and cargo in lower cargo compartment 306. Sensor systems 102 are configured to monitor systems and components within range of reader 308. In at least some embodiments, sensor systems 102 include sensors 112 that are selected with properties capable of detecting an/or measuring passenger activity and chemical, biological, and radioactive agents that may be carried or otherwise transported into passenger compartment 304.

Figure 4:
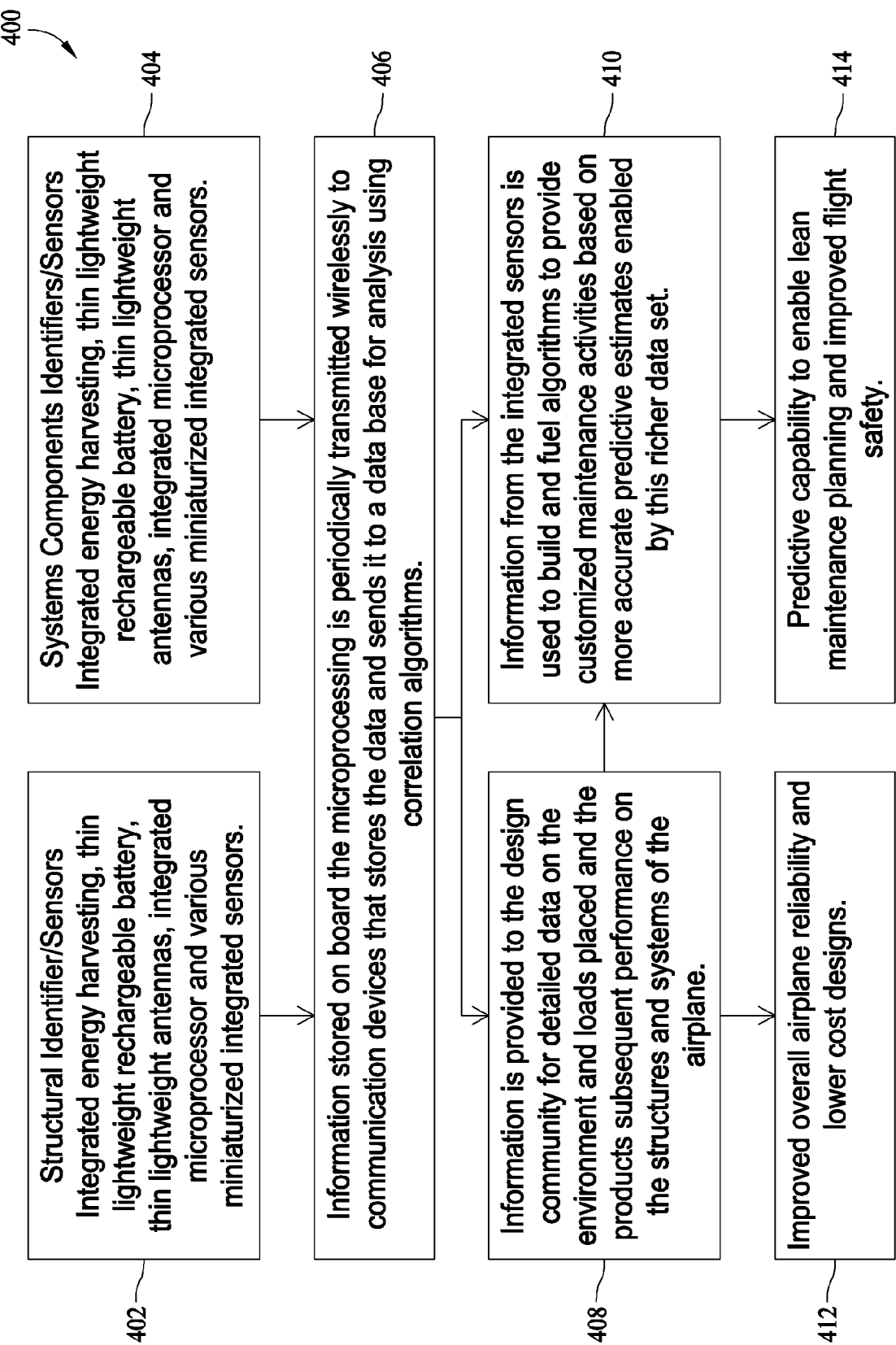
FIG. 4 is a flow diagram of an exemplary information generation flow for Structure and Systems Health Monitoring System (SSHMS) shown in FIG. 1.

FIG. 4 is a flow diagram 400 of an exemplary information generation flow for Structure and Systems Health Monitoring System (SSHMS) 100 (shown in FIG. 1). Structural sensor systems 402 include integrated energy harvesting, thin lightweight rechargeable battery, thin lightweight antennas, integrated microprocessor and various miniaturized integrated sensors mounted on a flexible substrate formed in some embodiments into an appliqué having a self-adhesive backing. Energy may be harvested from electromagnetic radiation received from for example, a reader onboard processing system 104, a piezo device using vibrations inherent in the mounted location, or converting thermo energy into electrical energy onboard the sensor system.

Systems/components sensor systems 404 include integrated energy harvesting, thin lightweight rechargeable battery, thin lightweight antennas, integrated microprocessor and various miniaturized integrated sensors. Information stored on board the microprocessors is periodically transmitted 406 wirelessly to communication devices that store the data and further transmits the data to a database for analysis using correlation algorithms. Information is provided 408 to the design community for detailed data on the environment and loads placed and the products subsequent performance on the structures and systems of the airplane. Information from the integrated sensors is used 410 to build and fuel algorithms to provide customized maintenance activities based on more accurate predictive estimates enabled by this richer data set. Improved 412 overall airplane reliability and lower cost designs result from awareness of the contextual relationships of the events and activities occurring with the structure and system components, which also provides more accurate predictive capability 414 to enable lean maintenance planning and improved flight safety.

The above-described methods and systems for monitoring aircraft structures and system components are cost-effective and highly reliable. The methods described herein utilize small lightweight sensors with embedded local micro-processing for collecting, deciphering and recording data along with wireless communication capability. Such wireless-enabled/smart-sensors/identifiers permit acquiring specific environmental and performance data for the components that encompass the entire aircraft wide component set. This data is then integrated to determine a detailed understanding of how the performance and environment of each of the components impacts the overall health of the set of components that make up the entire airplane.

While the invention has been described in terms of various specific embodiments, those skilled in the art will recognize that the invention can be practiced with modification within the spirit and scope of the claims.

What is claimed is:

1. A structural and component health monitoring system comprising:
   a plurality of sensor systems positioned about an object to be monitored;
   a processing system communicatively coupled to at least one of said plurality of sensor systems, said processing system comprises:
   an ontology and reasoning module configured to model the object to be monitored, reason about the received sensor data associated with the object to be monitored and reason about the relationships between the received sensor data to fuse the data into contextual information for the overall object to be monitored; and
   a contextual analyzer configured to transmit the received sensor data to said ontology and reasoning module and to store the information into a contextual information database.

2. The system in accordance with claim 1 further comprising a data acquisition module and sensor controller that permits said data acquisition module to retrieve real time and historical sensor data and contextual information from said sensor system.

3. The system in accordance with claim 1 further comprising a discovery module comprising at least one of a node discovery, a service discovery, and contextual information discovery wherein said node discovery is configured to determine a presence of a node, wherein said service discovery is configured to determine a service provided by the determined node, and wherein said contextual information discovery is configured to determine information relevant to the current context.

4. The system in accordance with claim 1 further comprising a contextual information database configured store sensor data fused by said ontology and reasoning module into contextual information for the overall object to be monitored.

5. The system in accordance with claim 1 further comprising an array sensing algorithm module comprising logic that governs at least one of the order in which specific sensor systems are interrogated and the periodicity of their respective interrogations.

6. The system in accordance with claim 1 further comprising a situation awareness analyzer configured to determine a present state of the object to be monitored, generate notification alerts in real time, and receive current and past contextual information generated by a contextual analyzer.

7. The system in accordance with claim 1 further comprising a situation awareness analyzer configured to receive discovery information from a discovery module, logic from the array sensing algorithm module, sensor data reported by a data acquisition module, and direct a sensor controller to interrogate a sensor system.

8. The system in accordance with claim 1 wherein said plurality of sensor systems comprises an ad hoc network configured to communicate sensor data between the plurality of sensor systems and an onboard processing system.

9. The system in accordance with claim 1 wherein at least one of said plurality of sensor systems comprises a flexible substrate.

10. The system in accordance with claim 1 wherein at least one of said plurality of sensor systems comprises an energy harvesting system.

11. The system in accordance with claim 1 wherein at least one of said plurality of sensor systems comprises a flexible film rechargeable battery.

12. The system in accordance with claim 1 wherein at least one of said plurality of sensor systems comprises a microprocessor that controls wireless communication between at least one of said sensor systems and an onboard processing system.

13. A method of monitoring the health of structures and system components, said method comprising:
   positioning a plurality of sensor systems proximate an object to be monitored, said sensor systems each including one or more sensors configured to detect object data that is related to the object health;
   wirelessly transmitting the data to at least one of another one of the plurality of sensor systems and a processing system; and
   analyzing the data to determine a contextual relationship between each of the plurality of sensor systems and the received data such that a present state of the object is determined.

14. The method in accordance with claim 13 further comprising:
   fusing data retrieved from a first sensor subsystem and a second sensor subsystem into a contextual form based on the sensor data type and sensor system location relative to the object and the others of the plurality of sensor systems at the time the data is sensed; and
   storing the fused data and the raw sensor data within a local storage device onboard said sensor system.

15. The method in accordance with claim 13 further comprising transmitting fused data and raw sensor data from the sensor system to the processing system in response to a command from the processing system.

16. A sensor networking system for monitoring the health of an aircraft structure and system components related to the aircraft, said system comprising:
   a plurality of sensor systems positioned about the aircraft, said sensor systems comprise a flexible substrate, an energy harvesting system, a rechargeable battery, and a microprocessor that controls wireless communication between at least one of said sensor systems and a processing system remote from said plurality of sensor systems, said plurality of sensor systems further comprising sensors including a plurality of different modalities; and
   a processing system communicatively coupled to at least one of said plurality of sensor systems, said processing system configured to receive at least one of sensor data and fused sensor data, said processing system comprising a situation awareness analyzer configured to determine an overall present state of the aircraft by observing the events and activities within the aircraft structure and aircraft systems using the plurality of sensor systems and correlating individual data elements and behavioral models to deduce overall system state and behavior.

17. The system in accordance with claim 16 wherein said situation awareness analyzer is further configured to generate notification alerts in real time, and receive current and past contextual information generated by a contextual analyzer.

18. The system in accordance with claim 16 wherein said situation awareness analyzer is further configured to receive discovery information from a discovery module, logic from the array sensing algorithm module, sensor data reported by a data acquisition module, and direct a sensor controller to interrogate a sensor system.

19. The system in accordance with claim 16 further comprising an ontology and reasoning module configured to model the aircraft structure and system components related to the aircraft, reason about the received sensor data associated with the aircraft structure and system components related to the aircraft and reason about the relationships between the received sensor data to fuse the data into contextual information for the overall aircraft structure and system components related to the aircraft.

20. The system in accordance with claim 16 further comprising a contextual analyzer configured to transmit the received sensor data to an ontology and reasoning module and to store the information into a contextual information database.

21. The system in accordance with claim 16 further comprising a data acquisition module and sensor controller that permits said data acquisition module to retrieve real time and historical sensor data and contextual information from said plurality of sensor systems.

22. The system in accordance with claim 16 further comprising a discovery module comprising at least one of a node discovery, a service discovery, and contextual information discovery wherein said node discovery is configured to determine a presence of a node, wherein said service discovery is configured to determine a service provided by the determined node, and wherein said contextual information discovery is configured to determine information relevant to the current context.

23. The system in accordance with claim 16 further comprising a contextual information database configured store sensor data fused by said ontology and reasoning module into contextual information for the overall aircraft structure and system components related to the aircraft.

24. The system in accordance with claim 16 further comprising an array sensing algorithm module comprising logic that governs at least one of the order in which specific sensor systems are interrogated and the periodicity of their respective interrogations.

25. The system in accordance with claim 16 wherein said plurality of sensor systems comprises an ad hoc network configured to communicate sensor data between the plurality of sensor systems and an onboard processing system.

* * * * *